United States Patent

Gilman et al.

[11] Patent Number: 5,951,505
[45] Date of Patent: *Sep. 14, 1999

[54] WOUND DRESSING AND DELIVERY SYSTEM THEREFOR

[75] Inventors: Thomas H. Gilman, Spring Grove; Robert W. Cramer, Lincolnshire, both of Ill.; James W. Humphries, Waynesboro, Va.

[73] Assignee: Hollister Incorporated, Libertyville, Ill.

[*] Notice: This patent issued on a continued prosecution application filed under 37 CFR 1.53(d), and is subject to the twenty year patent term provisions of 35 U.S.C. 154(a)(2).

[21] Appl. No.: 08/596,468

[22] Filed: Feb. 5, 1996

[51] Int. Cl.$^6$ ........................................... A61F 13/00
[52] U.S. Cl. ..................... 602/41; 602/42; 602/47; 602/57; 602/58; 128/888
[58] Field of Search .................. 602/41–58; 128/887, 128/888, 889

[56] References Cited

U.S. PATENT DOCUMENTS

| | | |
|---|---|---|
| 2,969,057 | 1/1961 | Simmons . |
| 4,598,004 | 7/1986 | Heinecke . |
| 4,600,001 | 7/1986 | Gilman . |
| 4,614,183 | 9/1986 | McCracken et al. . |
| 4,738,257 | 4/1988 | Meyer et al. ............................ 602/48 |
| 5,000,172 | 3/1991 | Ward . |
| 5,088,483 | 2/1992 | Heinecke . |
| 5,099,832 | 3/1992 | Ward ........................................ 602/57 |
| 5,106,629 | 4/1992 | Cartmell et al. . |
| 5,336,162 | 8/1994 | Ota et al. . |
| 5,423,737 | 6/1995 | Cartmell et al. . |
| 5,489,262 | 2/1996 | Cartmell et al. ......................... 602/52 |
| 5,709,651 | 1/1998 | Ward ........................................ 602/57 |

OTHER PUBLICATIONS

International Publication WO 94/14393.
European Pub. Appl. 0 630 629.
European Pub. Appl. 0 568 401.

*Primary Examiner*—Richard J. Apley
*Assistant Examiner*—Kim M. Lee
*Attorney, Agent, or Firm*—Tilton Fallon Lungmus

[57] ABSTRACT

A wound dressing is disclosed in which a pressure-sensitive adhesive layer, preferably of a soft, pliant adhesive composition having one or more hydrocolloids dispersed therein, is backed by an elastomeric film and has its opposite (bodyside) surface covered by a removable primary release sheet and a release strip, with at least a portion of the release strip being interposed between the adhesive layer and the primary release sheet along one side edge of the dressing. The primary release sheet and the release strip have superposed or overlapping tab portions that project outwardly beyond a side edge portion of the dressing. In a preferred embodiment, the adhesive and backing layers are translucent and the release strip is visible therethrough by reason of sharp color or tonal contrast in relation to the primary release sheet.

4 Claims, 2 Drawing Sheets

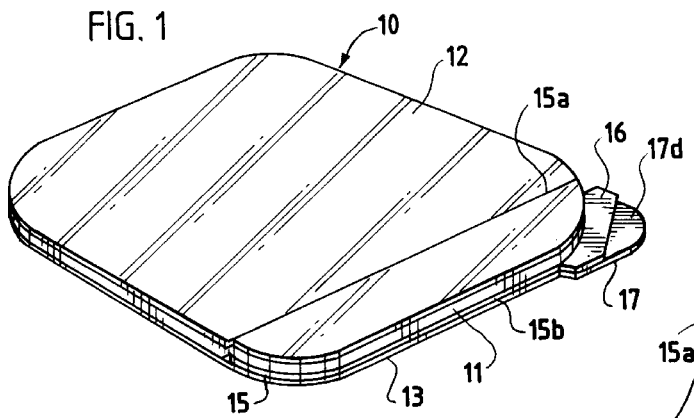
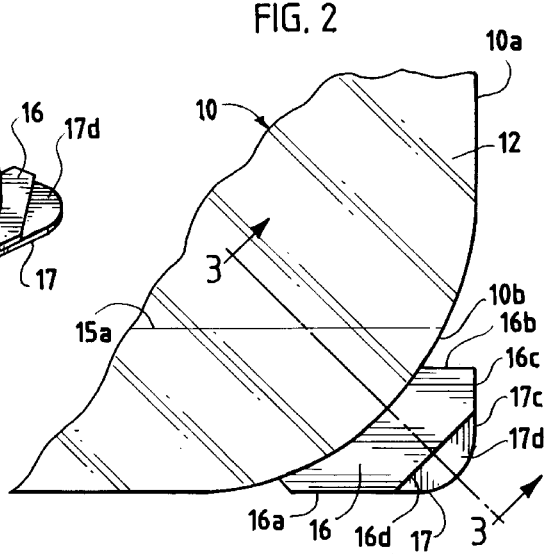
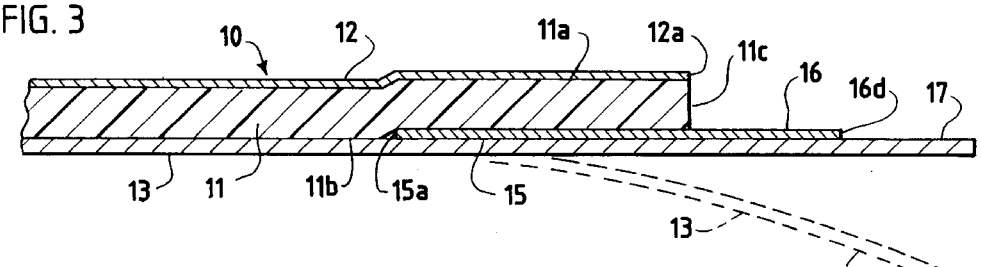
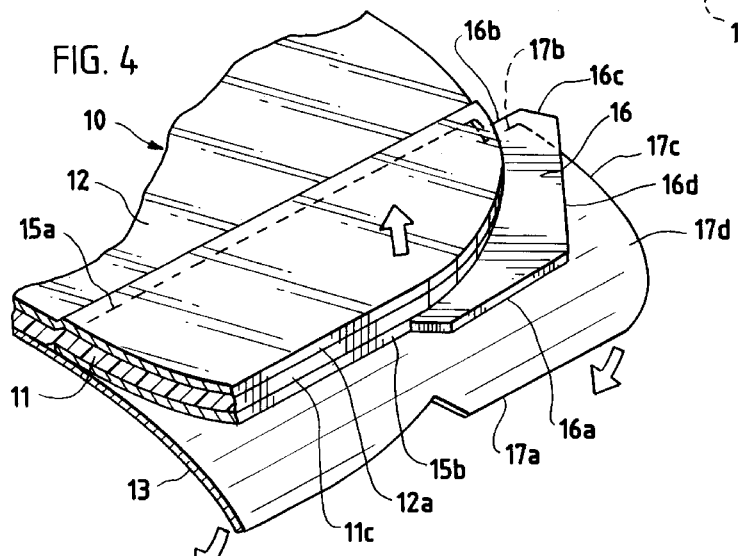
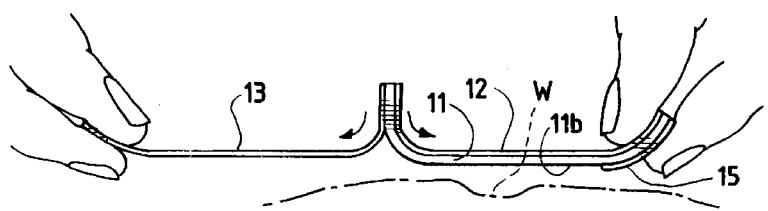

WOUND DRESSING AND DELIVERY SYSTEM THEREFOR

BACKGROUND AND SUMMARY

Wound dressings are known in which an adhesive layer is backed by a film of polyurethane or other suitable polymeric film and in which the bodyside surface (the wound-contacting surface) is covered by two or more removable release sheets. Each release sheet covers only a portion of the bodyside surface of the adhesive layer, with each sheet usually being butterfly folded to present diverging flaps extending along the line of meeting. Such flaps are used to grip the release sheets and peel them away from each other to expose the adhesive layer, and it has also been found convenient to utilize such flaps, after they have been partially removed, as preliminary gripping means for orienting the dressing and applying it to a wound site. One disadvantage of such a construction lies in the fact that the release sheets may not completely cover the adhesive surface of the dressing along the line of meeting, thereby creating the possibility that a narrower surface portion of the adhesive may be subject to deterioration and possible contamination during storage and application.

Such problems may be reduced by reversely-folding only one of the two release sheets as disclosed, for example, in U.S. Pat. No. 4,598,004. The advantages of such a construction are offset, however, by the fact that the release covering is then of triple thickness along one side of the fold line, usually creating a noticable step in the adhesive and backing layers overlying the fold. That disadvantage is compounded if the adhesive layer is a soft, pliant, fluid-absorbing, hydrocolloid-containing composition of a type now commonly used for wound dressings because, in such a case, the adhesive layer may become significantly deformed prior to application of the dressing and the effectiveness of the dressing in protecting a wound and absorbing exudate may be compromised. While the step effect might be reduced by omitting the reverse fold from one of the release sheets, so that only a double thickness of release sheet material exists along that portion overlapped by the flap of the other release sheet, the benefits of providing double flaps for ease of application, and to facilitate removal of both sheets, are then lost or at least diminished.

Other references illustrating the state of the art are U.S. Pat. Nos. 5,000,172, 5,336,162, 5,106,629, 5,423,737, 4,614,183 and 2,969,057.

One aspect of this invention lies in providing a wound dressing, preferably a dressing in which the adhesive layer is of a fluid-absorbing hydrocolloid-containing adhesive composition, utilizing a delivery system that overcomes the aforementioned defects and disadvantages of the prior art. In a dressing embodying this invention, the release sheet means takes the form of a primary release sheet and a release strip that cover the entire bodyside surface of the adhesive layer, with at least a portion of the release strip being interposed between the primary release sheet and a part of the bodyside surface along an outer edge portion of the dressing. Both the primary release sheet and the release strip are formed of flexible stretch-resistant sheet material and have their opposing surfaces unsecured to each other or at least readily separable from each other. Of particular importance in a preferred embodiment is the fact that both the primary release sheet and the release strip have tab portions that are superposed and project outwardly beyond the outer limits of the adhesive layer to assist a user in initiating a peeling back of the primary sheet and strip and to facilitate application of the dressing to a wound site.

The backside of the adhesive layer is covered by an elastomeric backing film. Ease of application of the dressing is further enhanced by reason of the adhesive layer and backing film being formed of translucent material and the release strip and primary release sheet (visible through the backed adhesive layer) being of contrasting colors or tones. Ideally, the primary release sheet is of a neutral color (white or whitish) and the release strip is of a darker contrasting color. In one embodiment, the tab portion of the release strip is smaller than the tab portion of the primary release sheet directly below and, because of the color or tonal contrast, a user may readily distinguish the two tab portions and urge them apart in commencing the steps of preparing the dressing for application. In a second embodiment, it is the tab portion of the release strip that is the larger of the two and, again, separation of the release sheet and release strip is facilitated by the color or tonal contrast.

While the planar wound dressing may assume different configurations, in a preferred embodiment the dressing is generally rectangular in outline with straight side edges and rounded corners, and the release strip extends along one of the side edges of the dressing. In such a construction, the superposed tab portions are preferably located at one of the rounded corners of the dressing and project outwardly therefrom.

An additional advantage of the dressing as so described is that in production it may be cut into its final shape in a single die-cutting operation, thereby eliminating many of the costs associated with the production of dressings requiring multiple die-cutting steps. To facilitate single-step cutting operations, it has been found desirable to form the release strip with parallel longitudinal side edges and with the tab portion of the strip (and also the underlying tab portion of the primary release sheet) extending endwise from the strip. Edges of the two tab portions nearest the inboard longitudinal edge of the release strip are offset in an outward direction from that inboard edge to assure completeness of cutting during the one-step cutting operation.

Other features, advantages and objects of the invention will become apparent from the specification and drawings.

DRAWINGS

FIG. 1 is a perspective view of a wound dressing embodying this invention.

FIG. 2 is an enlarged, fragmentary top plan view of a corner portion of the dressing.

FIG. 3 is a greatly enlarged sectional view taken along line 3—3 of FIG. 2.

FIG. 4 is a perspective view of the corner portion of the dressing depicted in FIGS. 2 and 3 with a portion of the primary release sheet being urged away from the protective release strip.

FIG. 5 is a somewhat schematic end view depicting a step in the preferred mode of applying the dressing to a wound site.

DETAILED DESCRIPTION OF PREFERRED EMBODIMENT

Figure 6:
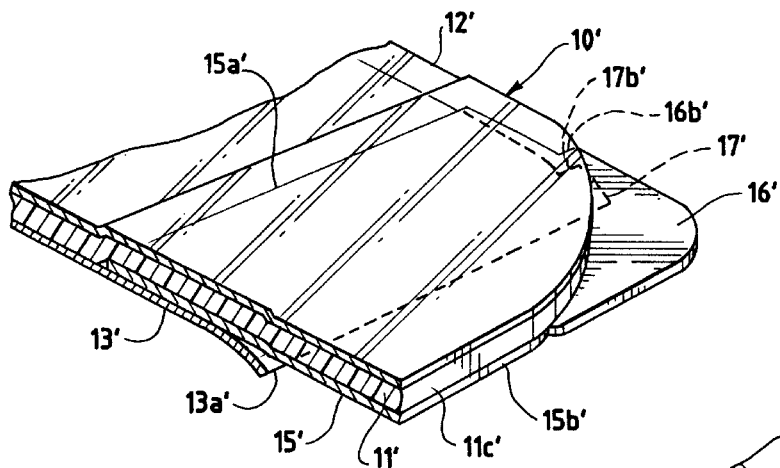
FIG. 6 is a fragmentary perspective view of the corner portion of a dressing constituting a second embodiment of the invention.
Figure 7:
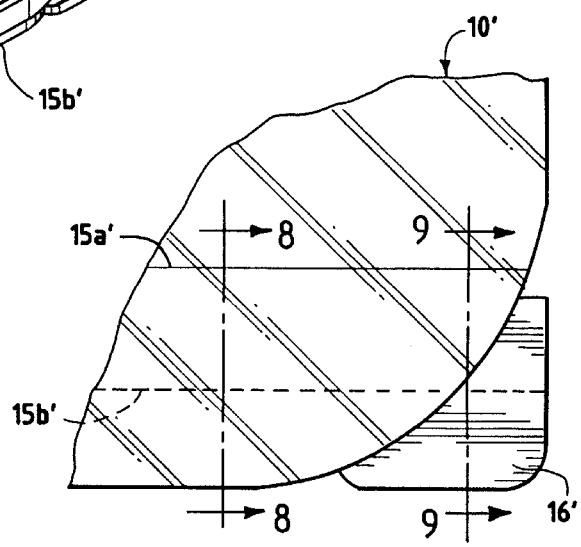
FIG. 7 is a top plan view of the corner portion of FIG. 6.
Figure 8:
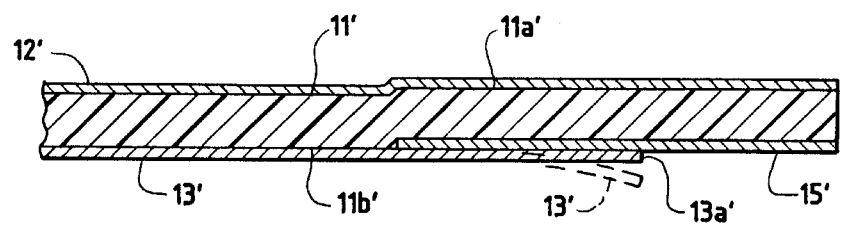
FIG. 8 is an enlarged sectional view taken along line 8—8 of FIG. 7.
Figure 9:
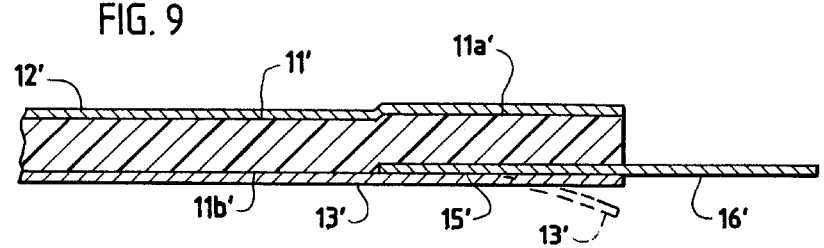
FIG. 9 is an enlarged sectional view taken along line 9—9 of FIG. 7.

In the embodiment depicted in FIGS. 1–5 of the drawings, the numeral 10 generally designates a wound dressing having an adhesive layer 11, a backing layer 12 that covers the top or backside 11a of the adhesive layer and is coextensive therewith, and release sheet means 13, 15 protecting the bodyside surface 11b of the adhesive layer, such release sheet means also being useful in the delivery and application of the dressing to a wound site.

The adhesive layer is preferably composed of a soft, pliant adhesive material that has both dry and wet tack and is capable of absorbing wound exudate. Such compositions are well known in the art and generally comprise homogeneous blends of one or more pressure-sensitive adhesive materials and one or more water-dispersible hydrocolloid materials. Other components such as tackifiers and plasticizers may be included, as well as one or more thermoplastic elastomers and/or one or more cohesive strengthening agents.

Suitable pressure-sensitive adhesive materials for inclusion in the adhesive layer are various natural or synthetic viscous or elastomeric substances such as polyisobutylene, polyurethane rubber, silicone rubber, acrylonitrile rubber, natural rubber, and the like. Thermoplastic elastomers may be included to impart properties of rubber-like extensibility and both rapid and complete recovery from modular strains to the pressure-sensitive adhesive component. Such elastomers include butyl rubber, styrene-isoprene-styrene copolymers, styrene-butadiene-styrene copolymers, and the like.

Suitable hydrocolloid materials that may be used in formulating the adhesive layer include sodium or calcium carboxymethylcellulose, pectin, gelatin, guar gum, locust bean gum, colagen and gum karaya. Super-absorbent type hydrocolloids may also be included. Such super-absorbents can be formed from starch and acrylonitrile, the starch, either gelatinized or in granule form, being reacted with acrylonitrile under alkaline conditions. For example, the resulting products may comprise a starch-polyacrylonitrile graph polymer, as described in U.S. Pat. Nos. 3,997,484 and 3,661,815. Synthetic super-absorbents may also be utilized, such as sodium polyacrylates.

For examples of moisture-absorbing and swellable adhesive compositions suitable for use in the wound dressing of this invention, reference may be had to U.S. Pat. Nos. 4,738,257, 4,231,369, and 4,538,603. While any of a number of such compositions might be used, particularly effective results have been obtained with a composition as disclosed in co-owned copending application Ser. No. 08/262,789, filed Jun. 20, 1994, now U.S. Pat. No. 5,492,943, the disclosure of which is incorporated by reference herein. Such an adhesive composition is an elastomer blend composed essentially of one or more high molecular weight polyisobutylenes and one or more styrene block copolymers. Included in the composition is a plasticizer of either petrolatum or mineral oil, a tackifier, and a small percentage of an antioxidant. The water-absorbing and swellable hydrocolloids constitute about 35 to 65% of the composition and are selected from the group consisting essentially of sodium carboxymethylcellulose and pectin, or mixtures thereof, and optionally include minor amounts of other hydrocolloid gums.

Backing layer 12 is thin, flexible, and preferably stretchable and recoverable. An elastomeric polyurethane film of about 0.5 to 1.5 mils in thickness is believed particularly effective although films formed of other materials such as polyester copolymers, elastomeric nylon block copolymers, and low density polyethylene may be used. In any event, it is particularly desirable that both the backing layer and the adhesive layer be translucent. The term "translucent" is here used to mean that the combined layers have sufficient transparency to permit release sheets of sharply contrasting colors and/or tones to be visually distinguishable therethrough. Taken together, the adhesive and backing layers comprise the basic layers of a wound dressing to be delivered to and applied at a wound site, but it is to be understood that additional layers of other materials may be included as needed or desired.

The adhesive and backing layers are coextensive, their continuous outer edges 11c and 12a being coincident. In the illustration given, the dressing is generally rectangular in outline with straight sides 10a and rounded corners 10b, but it is to be understood that other shapes may be selected as desired.

The release sheet means takes the form of a primary release sheet 13 and a narrow release strip 15. Release sheet 13 is preferably formed of siliconized paper and covers the entire bodyside surface 11b of adhesive layer 11. Release strip 15 may also be formed of siliconized paper, although a thin film of polyethylene or other polymeric material, composed or surface treated to resist strong adherence to adhesive layer 11, may be used. Both the sheet 13 and strip 15 should be flexible, tough and substantially non-stretchable.

As shown most clearly in FIG. 3, release strip 15 is interposed between release sheet 13 and adhesive layer 11 along one side edge of the dressing. Because the strip is thin (it preferably has a thickness no greater than about 5 mil) and is unfolded, it does not produce a significant step in the adhesive and backing layers thereabove or substantially alter the planar condition of those layers.

Release strip 15 has a pair of longitudinal edges 15a and 15b, at least the innermost edge 15a being straight and preferably parallel with one side edge of the generally rectangular dressing. One end of the strip protrudes beyond the adhesive and backing layers to define a tab portion 16. That tab portion 16 overlies a similar outwardly-extending tab portion 17 of release sheet 13. Except for tab portions 16 and 17, neither the primary release sheet 13 nor the release strip 15 extend beyond the edges of the adhesive and backing layers.

Tab portions 16 and 17 may be any of a number of shapes as long as each has a portion of substantial length extending along the side edge portions of the adhesive layer 11 and backing layer 12 directly thereabove. In the illustration given, tab portion 17 has parallel side edges 17a and 17b and an outer edge 17c at generally right angles thereto, with edges 17a and 17c merging along a curved or rounded corner. Similarly, tab portion 16 has parallel side edges 16a and 16b, and end edge 16c. An angular edge 16d extends from edges 16a to 16c so that tab portion 16 is smaller than tab portion 17. When the dressing is viewed from its topside or backside, a rounded corner portion 17d of the lower tab portion 17 is thereby exposed (FIG. 2).

While the location of the tab portions 16 and 17 might be other than as shown in the drawings, it is believed particularly desirable to locate such tab portions at a corner of the dressing since such location results in greater force concentration along the line of adhesive contact with layer 11 at the commencement of a peeling action. Such a location also results in the tab portion 16 of release strip 15 being at the end of that elongated strip, with edges 16a and 16b being parallel with the longitudinal inboard edge 15a of the strip. While edge 16b might be an extension of edge 15a, it has been found particularly desirable to offset edge 16b from edge 15a as shown in FIG. 2. The offset relation insures that all of the outer edges of the dressing, including the edges of the adhesive and backing layers and those of the release sheet 13, release strip 15, and tab portions 16 and 17, may be cut simultaneously in a single die-cutting operation.

The release strip 15 and its integral tab portion 16 should be opaque and of a color or tone that renders it readily distinguishable through the translucent adhesive and backing layers 11 and 12, respectively. The primary release sheet 13 is also preferably opaque although, if desired, it may be translucent or transparent. If opaque, it should be of a color or tone that contrasts sharply with that of the release strip 15, with such contrast being visually evident through the translucent upper layers of the dressing. It is particularly desirable that the inner longitudinal edge 15a of release strip 15 be visible through the translucent upper layers and that the color or tone of the primary release sheet 13 should not obscure such visibility. In a preferred mode of practicing the invention, the primary release sheet 13 is white or whitish in color (or some other neutral shade) and release strip 15, along with its integral tab, is of a dark tone such as a dark grey, dark brown, or a dark primary or secondary color, or even black. The sharp contrast between the primary release sheet 13 and release strip 15 is easily discernible through the translucent upper layers of the dressing and also makes it evident to a user that there are in fact two tab portions projecting outwardly from the remainder of the dressing, since the light toned corner portion 17d of the lower tab portion 17 extends outwardly beyond edge 16d of the upper darkly toned or colored tab portion 16.

In preparing the dressing for application to a wound site, a user simply grips the exposed corner 17d of the tab portion 17 and folds the primary release sheet 13 away from release strip 15 along a fold line parallel with the inner longitudinal edge 15a of the release strip. Such folding action is easily accomplished because the opposing surfaces of the release sheet and release strip are not adhered to each other and their composition or surface treatment resist such adherence. Gripping the dressing as depicted in FIG. 5, the user then peels the primary release sheet 13 away from the bodyside surface 11b of adhesive layer 11. While such peeling action may be easily accomplished, the adhesive resistance is sufficiently great that the dressing may be supported in the condition depicted in FIG. 5, allowing the user to locate the sterile bodyside surface of adhesive layer 11 over a wound site W. After the dressing has been lowered into contact with the wound site, release sheet 13 is completely peeled away from adhesive layer 11. The user then grips the exposed tab portion 16 of release strip 15 and peels the release strip away from the remainder of the bodyside surface 11b of the adhesive layer.

FIGS. 6–9 illustrate a second embodiment of the invention in which the wound dressing 10' is essentially the same as the dressing already described except for the release sheet means. The adhesive layer 11' could be of the same composition as layer 11 and has its top or backside 11a' covered by a backing layer 12' that is coextensive with the adhesive layer and may be substantially identical to backing layer 12 already described.

In the second embodiment, the primary release sheet 13' and the release strip 15' together cover the entire bodyside surface 11b of the adhesive layer. Release strip 15' is essentially the same as strip 15 and includes a tab portion 16' at one end. The release strip also has parallel longitudinal edges 15a' and 15b'. However, in the embodiment of FIGS. 6–9, the primary release sheet 13' is not coextensive with the bodyside surface 11b' of the adhesive layer but instead has one edge 13a' that is set back from the edge portion 11c' of the adhesive layer along the length of release strip 15'. In the illustration given, edge 13a' is straight and generally parallel with the edges 15a' and 15b' of the release strip 15'. As before, the release strip 15' extends between the adhesive bodyside surface 11b' and the primary release sheet 13'; however, in this embodiment, only a portion of the release strip is interposed between the adhesive layer and the primary release sheet. Since the opposing surfaces of the primary release sheet and the release strip are unsecured to each other, a user may easily grasp the primary sheet by its free edge portion 13a', or by its tab portion 17', to commence peeling the primary release sheet away from the remainder of the dressing.

As shown most clearly in FIG. 6, the tab portion 16' of the release strip is larger than the tab portion 17' of the primary release sheet. Because of their contrasting colors or tones, a user may readily observe the free edge or tab portions of the primary release sheet and commence a peeling back of that sheet. Such color or tonal contrast also renders the release strip visible through the translucent adhesive and backing layers 11 and 12 in the same manner as previously described.

As in the first embodiment, the tab portions have die-cut edges 16b' and 17b' that are offset from the longitudinal inner edge 15a' of the release strip 15' to assure completeness of cutting during a one-step die-cutting operation.

While in the foregoing we have disclosed embodiments of the invention in considerable detail for purposes of illustration, it will be understood by those skilled in the art that many of these details may be varied without departing from the spirit and scope of the invention.

We claim:

1. A wound dressing comprising a soft, pliant adhesive layer having bodyside and backside surfaces and a continuous outer edge; a thin, flexible backing layer covering said backside surface and having an outer edge coincident with said outer edge of said adhesive layer; said backing layer having an exposed surface facing away from said adhesive layer; and removable release sheet means including a primary release sheet extending along said bodyside surface and covering said bodyside surface in its entirety and a thin, planar unfolded release strip interposed between said primary release sheet and a part of said bodyside surface along an outer edge portion of said adhesive layer; said adhesive layer comprising a homogenous blend of an elastomeric adhesive material and particles of one or more water-absorbing and swellable hydrocolloid materials dispersed therein, said primary release sheet and said release strip being formed of flexible, stretch-resistant sheet material and having overlapping tab portions projecting outwardly beyond said outer edges of said adhesive and backing layers; said backing and adhesive layers being translucent and said release strip being opaque and visible through said backing and adhesive layers; said tab portion of said release strip being smaller in outline than said tab portion of said primary release sheet so that a part of the tab portion of the primary release sheet is accessible from a direction of the exposed surface of the flexible backing layer of the wound dressing.

2. The dressing of claim 1 in which said release strip and said primary release sheet are of contrasting colors or tones.

3. The dressing of claims 1 or 2, in which said dressing is generally rectangular in outline with straight edges and rounded corners; said release strip extending along one of said straight side edges of said dressing; and said superposed tab portions being located at one of said rounded corners of said dressing.

4. The dressing of claim 3 in which said release strip has longitudinal inner and outer edges; said tab portions having at least one coincident edge offset outwardly from said longitudinal inner edge of said release strip.

* * * * *